United States Patent [19]
Diaz et al.

[11] Patent Number: 5,349,869
[45] Date of Patent: Sep. 27, 1994

[54] WELDED NICKEL ALLOY DOUBLE-CANTILEVER BEAM CRACK GROWTH SENSOR AND METHOD FOR ITS FABRICATION

[75] Inventors: Thomas P. Diaz, San Martin; Gail E. Dunning, Sunnyvale; Ronald E. LeBlanc, San Martin, all of Calif.

[73] Assignee: General Electric Company, San Jose, Calif.

[21] Appl. No.: 43,052

[22] Filed: Apr. 5, 1993

[51] Int. Cl.⁵ .............................................. G01N 19/00
[52] U.S. Cl. .................................................... 73/799
[58] Field of Search .............. 73/799; 29/610.1, 621, 29/621.1; 228/103, 222

[56] References Cited
U.S. PATENT DOCUMENTS

| | | | |
|---|---|---|---|
| 4,677,855 | 7/1987 | Coffin, Jr. et al. | 73/799 |
| 4,924,708 | 5/1990 | Solomon et al. | 73/799 |

*Primary Examiner*—Robert Raevis
*Attorney, Agent, or Firm*—J. S. Beulick

[57] ABSTRACT

A double-cantilever beam crack growth sensor made from welded alloy, e.g., nickel-based alloy, and a method for fabricating such sensors. The method includes the steps of forming a strongback from a block of a first nickel-based alloy; depositing a suitable thickness of nickel-based weld alloy on top of the strongback to form a bi-metallic test block; welding a second block of the first nickel-based alloy on top of the weld alloy; and machining the final three-layer block to form a double-cantilever beam crack growth sensor consisting of cantilever beams made of the first nickel-based alloy, a crack growth section of weld alloy having a microstructure wherein the direction of dendritic growth is parallel to the direction of crack growth and a third section made of the first nickel-based alloy.

20 Claims, 3 Drawing Sheets

5,349,869

WELDED NICKEL ALLOY DOUBLE-CANTILEVER BEAM CRACK GROWTH SENSOR AND METHOD FOR ITS FABRICATION

FIELD OF THE INVENTION

This invention is directed to a method for fabricating sensors for measuring and monitoring damage to structural components within aggressive service environments. More particularly, it is directed to a method for fabricating double-cantilever beam sensors for measuring crack growth in structural components.

BACKGROUND OF THE INVENTION

When structural materials are exposed to particular aggressive service environments under steady or cyclic stress, the material will be susceptible to damage in the form of cracking. This type of damage is commonly referred to as "stress corrosion cracking" or "corrosion fatigue" (hereinafter "SCC"). It is desirable to monitor and assess the extent of damage to structural components due to SCC, for example, in a nuclear plant which has been operating for a number of years to help predict its lifetime. Methods for directly measuring crack growth in specimens removed from their environment are known. These methods use a variety of monitoring systems including visual and voltage potential drop methods.

U.S. Pat. No. 4,677,855 to Coffin et al. discloses a method for accurately assessing crack growth in structural components through voltage potential drop methods by establishing a reasonably accurate relationship between measured voltage and crack size. This patent discloses a sensor for measuring growth of a preformed crack within a solid exposed to an aggressive environment during application of a load. The crack is defined as possessing a mouth and a tip. The "mouth of the crack" is defined as the point or line of action of load application. The "crack tip" is the leading edge of the crack. The "length" of the crack is defined as the distance from the mouth of the crack to the crack tip. The preformed crack within the solid is of a known length. The size and shape of the preformed crack can vary widely; however, the cracks cannot be so large that the sensor will be separated into two sections.

The solid must be electrically conductive, such as carbon or alloy steel, nickel and nickel-based alloys, titanium and its alloys and structural materials such as austenitic stainless steels and the like. A current is passed through the solid to establish a voltage drop across the crack. This voltage is measured by at least two pairs of probes, the probes of each pair being positioned on opposite sides of the crack at equal, known distances from the mouth of the crack.

When a current is caused to flow through the sensor perpendicular to the crack, the potential difference between two points located on opposite sides of the crack will increase as the size of the crack increases. Measurement of the electric potential will provide information as to the instantaneous damage as well as the accumulated damage to the sensor in the form of crack growth. The measured voltage across each probe pair is plotted versus the distance from the crack mouth. A "best fit" curve or straight line of voltage versus the distance of the probe pairs from the crack mouth is drawn through these points and extrapolated to obtain the x-intercept, i.e., when the voltage will be zero. X-intercept values thus obtained are used to calculate the length of a propagating crack.

The sensor provides information which reflects on the condition of a particular structural component of interest. To achieve this purpose, it is preferable to manufacture this sensor from the same material with the same process history as the structural component of interest. When monitoring the damage to a structural component, the sensor is placed within the same environment as the structural component. The sensor then experiences the same changing environmental conditions as these structural components. The sensor is disposed in the aggressive environment, i.e., an environment which attacks the sensor material with sufficient severity to enhance the growth of the preformed crack, and the crack is supplied with a stress intensity at the crack tip which correlates to a stress intensity which the structural component experiences under operating conditions.

Although the sensor size, crack size and crack location can vary widely, the configuration of the sensor preferably permits a load of sufficient magnitude to be applied to the crack to provide a crack tip stress intensity factor that will allow the crack to grow at an appropriate rate. A sensor having a double-cantilever beam ("DCB") geometry permits a load of sufficient magnitude to be conveniently applied. As shown in FIG. 1, a sensor 10 with DCB geometry has two parallel arms (beams) 12 and 14 joined at one end and separated at the other. A slot or deep notch 16 separates the arms, and the base of this notch is referred to as the notch root 18. The preformed crack 20 is preferably positioned at the notch root. This configuration permits a number of measurements to be taken at various positions along the two beams 12, 14 since the effective crack length is extended along these beams. In addition, if the load remains constant, the stress intensity factor at the crack tip increases as the distance between the crack tip and the point of the load increases. Therefore, the long length of the sensor permits the threshold crack tip stress intensity to be obtained at low load levels.

Side grooves 34 placed within the sensor along the plane of the preformed crack determine the plane in which the crack grows. It is important to keep the fracture surfaces of the crack as planar as possible to avoid multiple cracking and bridging of the crack. Bridging can lead to a short circuit in the current flow and cause errors in the electric potential measurements.

For monitoring SCC in aggressive environments, an active load or a fixed displacement must be applied to the sensor. The means for applying a fixed displacement to cause the preformed crack to grow can be wedge 24 forced within the notch to expand the crack or other suitable means such as a clamp or bolt. The means for applying a fixed displacement must be made of electrically non-conductive material.

Crack growth is preferably monitored by measuring a potential or voltage across pairs of probes disposed along beams 12 and 14, and using such measured voltages, as well as the initial parameters, to calculate a crack length. Calculated crack lengths may advantageously be plotted as a function of time in order to assess a rate of crack growth. At least two pairs of probes are used to detect the voltage across the crack. However, at least three pairs of probes 26a/26b, 28a/28b and 30a/30b are preferred for accurate measurement of the crack growth. Each pair of probes is positioned at a different distance from the mouth of the crack, indicated in FIG. 1 as $X_1$, $X_2$ and $X_3$, respectively. The two probes of each pair are positioned on opposite sides of the crack, preferably an equal distance from the plane of the crack. The two probes of each pair are also equidistant from the mouth of the crack, i.e., they are the same distance from the leads 32a and 32b which supply a current to the sensor.

The sensor is supported in the aggressive environment by pressure coupling 36. Channel 38 provides access to channels (or holes) 40, both of which provide pathways for the conductive leads attached to the probe pairs and to conductive leads which preferably supply a d.c. potential to the sensor. The reversing direct current is supplied at points 32a and 32b and the effective initial length of the crack is indicated by dimension $a_O$.

SUMMARY OF THE INVENTION

The present invention is a DCB crack growth sensor made from welded alloy, e.g., nickel-based alloy, and the method for fabricating such sensors. The weld deposit of a nickel alloy DCB crack growth sensor fabricated using this method has a columnar/dendritic structure which is oriented in alignment with the desired direction of crack growth.

To produce a DCB crack growth sensor having a columnar/dendritic growth direction of the weld deposit aligned along the preferred direction of crack propagation, the method of the invention includes the following steps: form a strongback of suitable length, width and thickness from a block of a first type of nickel-based alloy; deposit a suitable thickness of nickel-based weld alloy on top of the base block of the strongback alloy to form a bi-metal test block, the weld alloy having a nickel-based composition different than that of the strongback alloy; mill the top surface of the weld alloy of the test block and prepare the milled surface for welding; weld a second block of nickel-based alloy of the first type of suitable thickness to the weld-prepped surface of the weld alloy; and machine the final three-layer block to form DCB crack growth sensors consisting of a first section of nickel-based alloy of the first type forming the arms of the DCB, a crack growth section of weld alloy with the proper columnar/dendritic orientation and a third section of nickel-based alloy of the first type.

BRIEF DESCRIPTION OF THE DRAWINGS

The preferred embodiments of the invention will be described in detail with reference to the drawings, wherein.

DETAILED DESCRIPTION OF THE PREFERRED EMBODIMENTS

Before conceiving the present invention, experiments were conducted in which nickel alloy DCB crack growth sensors were fabricated using material from a conventional weld deposit test block. Two laboratory-type DCB sensors were fabricated from Alloy 182. The composition of Alloy 182 is as follows: 59.0% Ni (min.), 13.0-17.0% Cr, 10.0% Fe (max.), 5.0-9.5% Mn, 1.0-2.5% (Cb+Ta), 1.0% Ti (max.), 1.0% Si (max.), 0.50% Cu (max.), 0.12% Co (max.) (when specified), 0.10% C (max.), 0.03% P (max.), 0.015% S (max.) and 0.50% others (max.).

Figure 1:
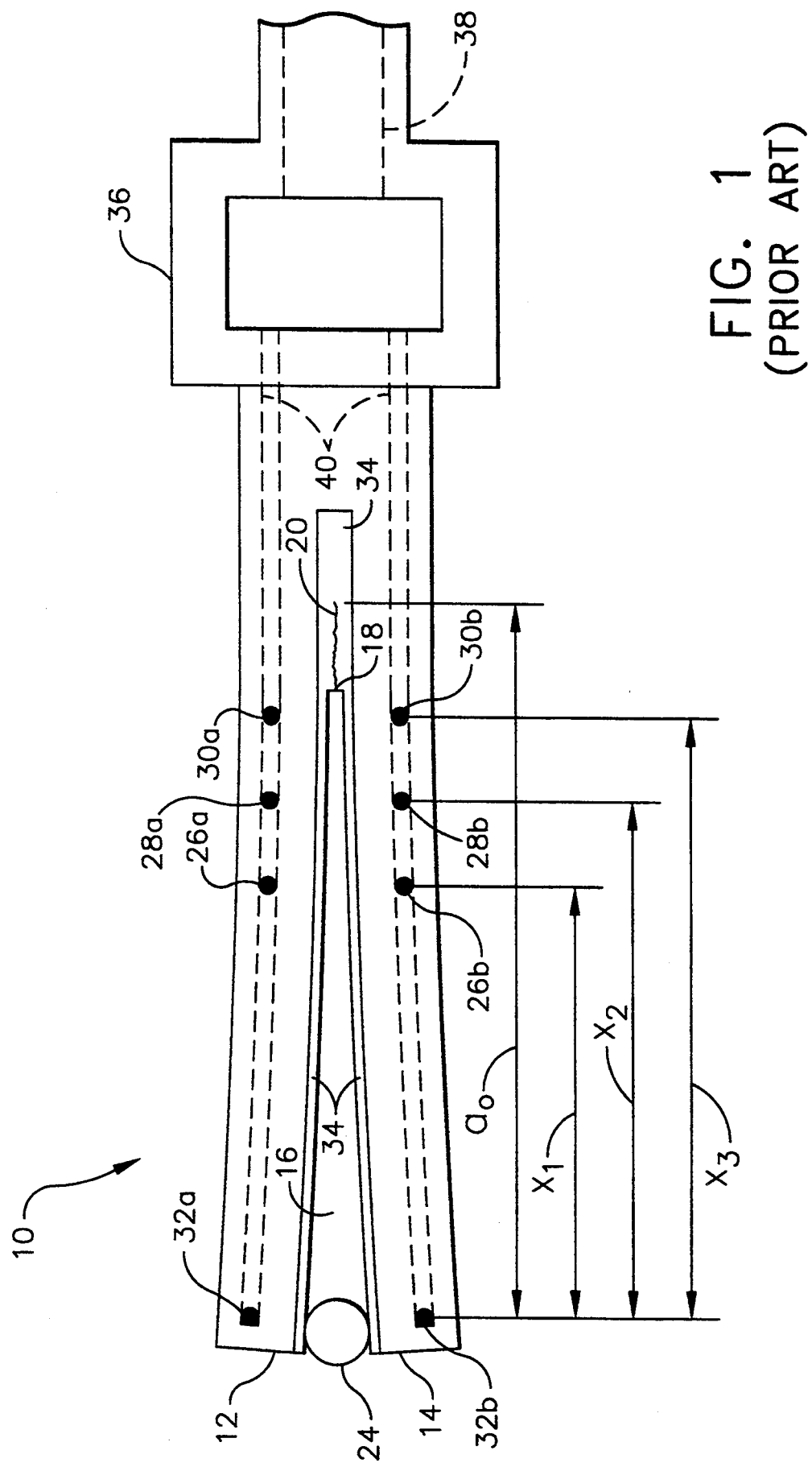
FIG. 1 is a schematic representation of a conventional DCB crack growth sensor.
Figure 2:
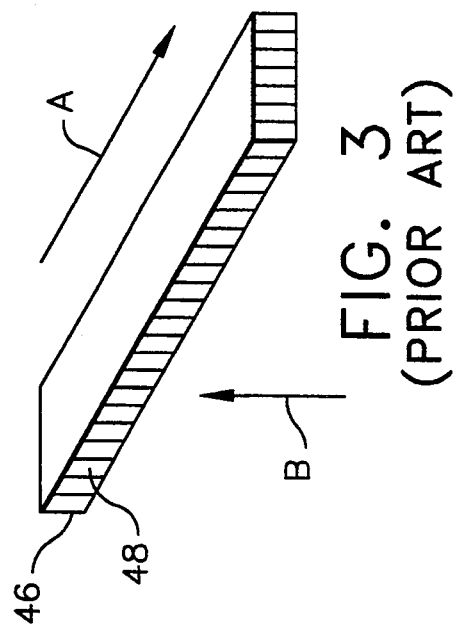
FIGS. 2 through 5 illustrate the fabrication of DCB crack growth sensors in which the direction of dendritic growth is perpendicular to the direction of crack growth.
Figure 3:
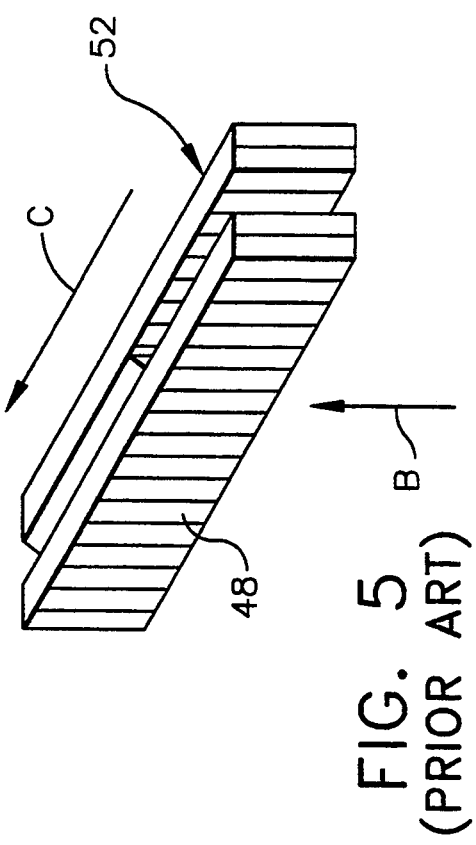

First, stainless steel plates 42 were welded to a carbon steel strongback 44 to form a channel having a length of 14 inches and a width of $3\frac{1}{2}$ inches (see FIG. 2). The channel is open at both ends and at the top. Alloy 182 (Heat 9023) was deposited (using an individual weld rod for each bead) in the channel until a block 46 approximately $3\frac{1}{2} \times 1\frac{1}{2} \times 14$ inches was obtained. The weld pass direction is indicated by arrow A in FIG. 3. The composition of Heat 9023 was determined by chemical analysis to be as follows: 68.54% Ni, 14.45% Cr, 7.54% Fe, 6.66% Mn, 1.50% Cb, <0.01 Ta, 0.60% Ti, 0.53% Si, 0.12% Cu, 0.046% C, 0.010% P, 0.002% S and 0.50% others.

During cooling of the Alloy 182 after deposition of the weld beads, the geometry of the channel and the carbon steel strongback 44 produce a heat sink which affects the solidification of the molten weld alloy. The molten Alloy 182 solidifies first at the strongback surface and then progressively vertically upward. This effect produces a columnar/dendritic microstructure perpendicular to the heat sink plane. The array of parallel lines in the figures is intended to symbolize the columns of dendrites 48 of this microstructure. The direction of dendritic growth is indicated by arrow B.

Figure 4:
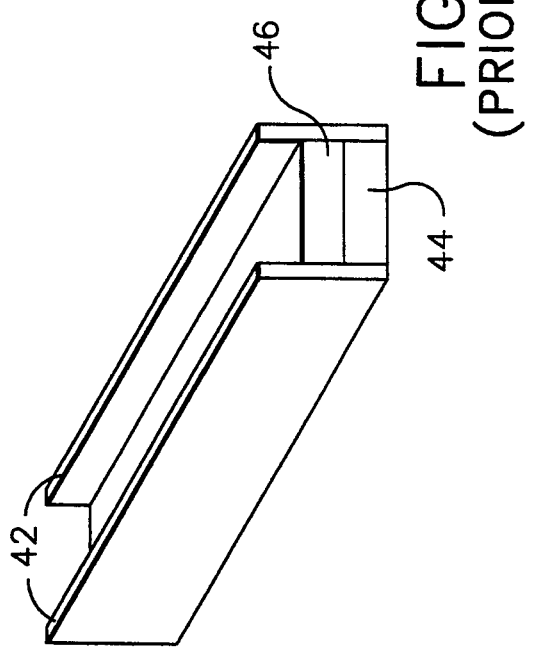
Figure 5:
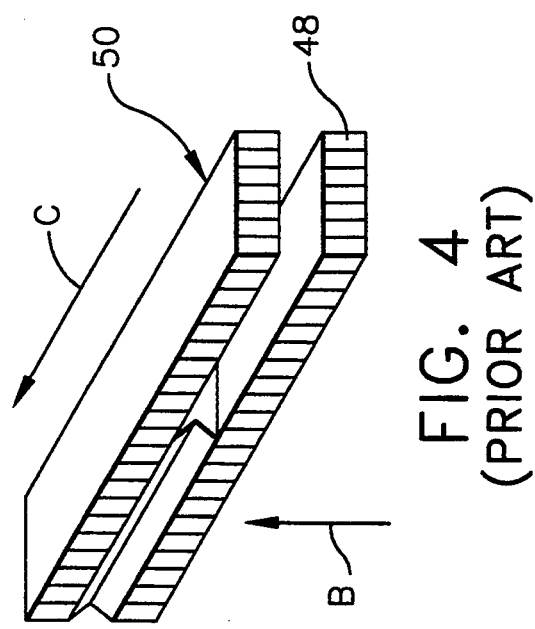

A post-weld heat treatment at 1150° F. for 24 hr followed. This experimental weld-deposited block was then milled to remove diluted regions, cut and machined as shown in FIGS. 4 and 5 to produce specimens 50 and 52. The direction B of columnar/dendritic growth in both specimens was perpendicular to the direction C of crack growth. In specimen 50 (FIG. 4), the direction of columnar/dendritic growth is perpendicular to the crack growth plane, whereas in specimen 52 (FIG. 5), the direction of columnar/dendritic growth is parallel to the crack growth plane.

Fatigue pre-cracking of both specimens was conducted in air at a mean load of 122.5 lbs. for 123,300 cycles to obtain a preformed crack length $A_t$ of 2.995 and 3.0097 inches for specimens 50 and 52 respectively. Following fatigue pre-cracking, specimen 50 was installed in a loading fixture. Initial exposure to produce environmental crack growth was in water containing 200 ppb $O_2$ under constant load, at a stress intensity of 28 Ksi·$\sqrt{}$inch. Due to the lack of measurable crack growth, the environment was changed to air-saturated water and the load was increased to 33 Ksi·$\sqrt{}$inch, which had no effect on the crack growth rate. Cyclic loading was then tried at 0.5 and 5 cph using a max./min. load ratio of R=0.7. $Na_2SO_4$ was also added to obtain a conductivity as high as 2.0 $\mu$S/cm. The growth rate under these severe conditions was 2.9 $\mu$inch/hr.

In view of the lack of success with specimen 50, specimen 52 was installed in the test fixture after receiving a 24-hr 932° F. sensitization heat treatment. The specimen was exposed to 1.6-2.0 $\mu$S/cm $Na_2SO_4$, 8 ppm $O_2$ water under constant load at a stress intensity of 28 Ksi·$\sqrt{}$inch, which produced a modest crack growth rate of $\approx$14 $\mu$inch/hr.

Additional testing was conducted in 200 ppb $O_2$ water using specimen 52, under cyclic loading (R=0.7) at K=33 Ksi·$\sqrt{}$inch The load was raised to 35 Ksi·$\sqrt{}$inch after 260 hr due to the slow (1.4 μinch/hr) growth rate in 200 ppb $O_2$ water. The maximum stable growth rate at the new load was 6.2 μinch/hr. Cycling of the specimen was suspended after 6247 hours. The virtual halt of crack growth under high constant load confirmed that the observed cracking was mostly the result of cyclic loading.

Visual inspection of specimen 50 side grooves showed that approximately 17 mils of growth had occurred, which contradicted the reversing d.c. data. In the case of specimen 52, the visible cracking in side groove B was longer than that of side groove A, and an average crack growth of 14 mils was calculated. After the side groove measurements were completed, specimen 52 was subjected to further fatigue cracking to extend the crack by about 0.75 inch. The specimen was then sectioned transverse to the long axis to expose the crack fracture surface. Photomicrography of the fracture surface showed the fatigue precrack, the environmentally produced cracking and the post-test fatigue crack. The maximum measured length of the environmental crack was 14 mils. This value correlated with the visual estimate of the side groove cracking. Environmental cracking occurred mostly along side groove B and a crack transverse to the specimen axis appeared to be present close to side groove A.

Figure 6:
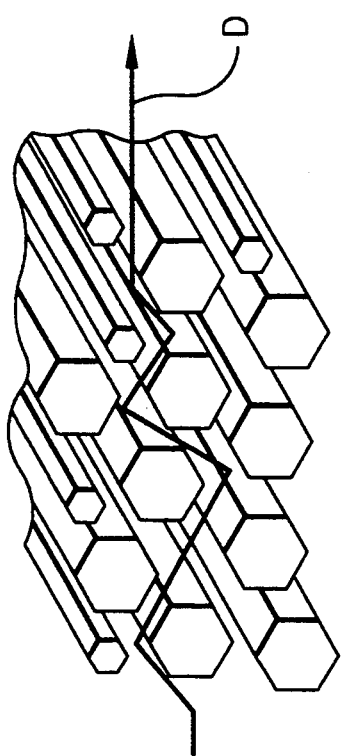
FIG. 6 is a schematic representation of a zig-zag crack growth path in a DCB crack growth sensor of the type shown in FIG. 5.

Specimen 50 was sectioned transverse to the long axis about ⅛ inch from the uncracked end to evaluate the microstructure. Photomicrography showed that the orientation of the columnar/dendritic microstructure was parallel to the ligament plane. However, the direction of columnar/dendritic growth during solidification was perpendicular to the direction of crack growth along the ligament length, which may have hindered crack growth by forcing the crack front to zigzag between columnar/dendritic boundaries in the manner depicted in FIG. 6.

Metallography of a longitudinal section of the ligament showed that the direction of columnar/dendritic growth in specimen 52 was perpendicular to the direction of the fatigue precrack. In this case, the misorientation of the crack plane with the microstructure was most likely the cause for the inhibited crack growth observed. Photomicrography revealed that a secondary crack propagated perpendicular to the crack growth plane defined by the fatigue precrack. The crack grew through the path of least resistance along columnar boundaries to a depth of approximately 55 mils. The crack tip was branched and mostly trans-dendritic, suggesting that a fatigue component was present in the later stages of cracking. The crack morphology of the environmentally produced cracking was very similar to the fatigue precrack and post-test fatigue cracking, indicating that the observed cracking during testing was a form of corrosion fatigue. The cracking was undoubtedly environmentally assisted since the more corrosive environments produced a higher crack growth rate, but, as previously discussed, crack growth virtually stopped without cycling.

In summary, specimen 50 showed insignificant crack growth in air-saturated water with $Na_2SO_4$ conductivity as high as 2.0 μS/cm. Specimen 52, which received an additional 24-hr sensitization heat treatment at 932° F., exhibited modest crack growth ($\approx$15 μinch/hr) in high-conductivity 8 ppm $O_2$ water. This led to the conclusion that the orientation of the microstructure with respect to the ligament plane is critical to the success of DCB specimens. In specimens 50 and 52, the columnar/dendritic grains in the microstructure were perpendicular to the direction of crack growth and acted as crack inhibitors. Since the crack growth direction of DCB specimens fabricated from conventionally deposited blocks will always be perpendicular to the columnar/dendritic growth axis of the material, optimum crack growth conditions cannot be achieved with such specimens.

This conclusion led to the conception of the vertical weld pad method of the invention. This method produces a weld buildup with dendrites correctly oriented in the direction of crack growth in a fabricated nickel alloy DCB crack growth sensor.

In carrying out the vertical weld pad method of the invention, 3/32-inch-diameter welding rods made of Alloy 182 (Heat 46471) were used. The composition of Heat 46471 was determined by chemical analysis to be as follows: 69.0% Ni, 14.5% Cr, 6.5% Fe, 6.7% Mn, 2.1% (Cb +Ta), 0.3% Ti, 0.8% Si, 0.00% Cu, 0.04% Co, 0.05% C, 0.00% P, 0.005% S and <0.50% others.

In the first step of the fabrication method, a 2.5-inch-thick block 54 of Alloy 600 was used as the strongback. The composition of Alloy 600 is as follows: 72.00% Ni (min.), 14.00–17.00% Cr, 6.00–10.00% Fe, 1.00% Mn, 0.50% Si, 0.50% Cu, 0.15% C and 0.015% S. A 2.75-inch-thick Alloy 182 weld pad 56 was built up on block 54. During solidification of the molten weld alloy, the Alloy 600 acts as a heat sink, causing the Alloy 182 dendrites 48 to form along the vertical axis.

Figure 7:
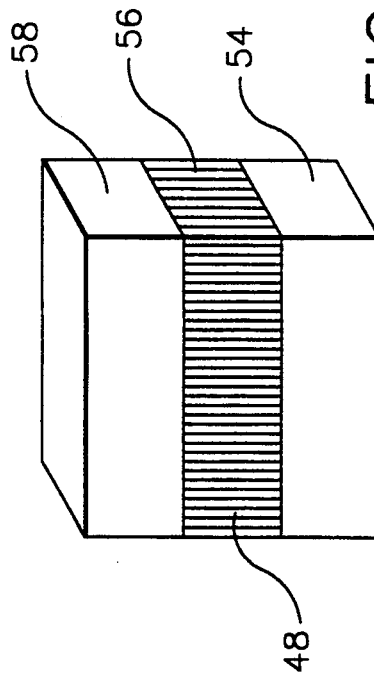
FIGS. 7 through 9 illustrate the fabrication in accordance with the invention of DCB crack growth sensors in which the direction of dendritic growth is parallel to the direction of crack growth.

After the weld alloy solidified, the bi-metallic block was milled and narrow grooves were machined on the Alloy 182 side to prepare the surface for welding. Another 2.75-inch-thick block 58 of Alloy 600 was then welded on top of the Alloy 182 weld pad. This configuration is shown in FIG. 7. A post-weld heat treatment of 1150° F. for 24 hr was performed and was followed by a sensitization heat treatment of 932° F. for 24 hr.

Figure 9:
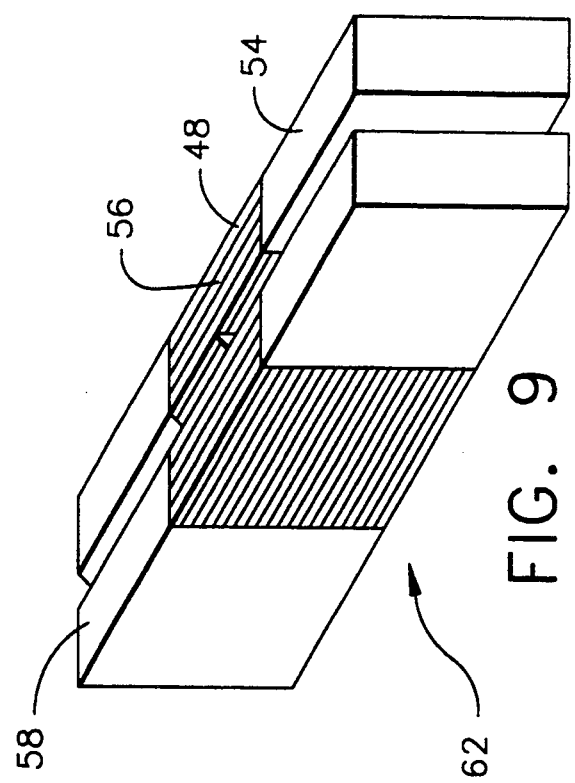
Figure 8:
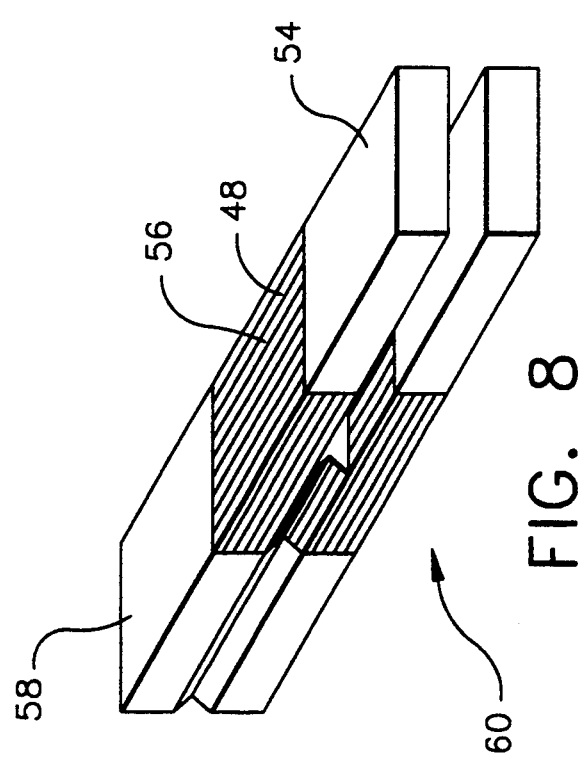

After the heat treatments, the three-layer block was machined in the vertical direction to form DCB specimens having three material regions. FIGS. 8 and 9 show the orientation of two machined DCB specimens 54 and 56, both of which have their dendrites 48 oriented parallel to the direction of crack growth. As a result, the dendrites do not inhibit crack propagation. Nickel alloy DCB crack growth sensors made in accordance with this method can be used to measure and monitor nickel alloy structural components placed in aggressive service environments.

In accordance with an alternative embodiment, a DCB crack growth sensor can be made by weld-depositing Alloy 182 on a strongback to form a vertical pad that has no Alloy 600. The weld deposit can be machined to form DCB sensors made entirely of Alloy 182 and having the desired columnar/dendritic orientation. As a result, the cantilever beams and the crack formation zone are both formed of Alloy 182.

Although the invention has been disclosed in the context of a preferred embodiment made from nickel-based alloys, DCB crack growth sensors can be made in accordance with the invention utilizing other kinds of alloys. The feature common to such sensors is that the direction of dendritic growth in the crack formation region is parallel to the direction of crack growth. Possible variations in the composition of the weld alloy used in practicing the invention will be readily apparent to practitioners skilled in the art. All such variations and modifications are intended to be encompassed by the claims set forth hereinafter.

We claim:

1. A double-cantilever beam crack growth sensor comprising first and second cantilever beams and a crack formation zone, each of said first and second cantilever beams having one end joined to said crack formation zone, said crack formation zone having a direction of crack growth opposite to the general direction in which said cantilever beams extend away from said crack formation zone, wherein said crack formation zone is made of an alloy of first type having a microstructure of dendrites which are substantially parallel to said preferred direction of crack growth.

2. The double-cantilever beam crack growth sensor as defined in claim 1, wherein said first and second cantilever beams comprise an alloy of second type different than said alloy of said first type.

3. The double-cantilever beam crack growth sensor ad defined in claim 2, wherein said alloy of said first type has a composition substantially similar to that of Alloy 182 and said alloy of said second type has a composition substantially similar to that of Alloy 600.

4. The double-cantilever beam crack growth sensor as defined in claim 2, further comprising a solid block of alloy of said second type welded to the side of said crack formation zone remote from said first and second cantilever beams.

5. The double-cantilever beam crack growth sensor as defined in claim 2, wherein said alloys of said first and second types have respective compositions which include first and second amounts of nickel respectively, said first and second amounts being different.

6. The double-cantilever beam crack growth sensor as defined in claim 1, wherein said first and second cantilever beams are made of said alloy of said first type.

7. The double-cantilever beam crack growth sensor as defined in claim 1, wherein said alloy of said first type is a weld alloy.

8. The double-cantilever beam crack growth sensor as defined in claim 7, wherein said crack formation zone comprises beads of said weld alloy.

9. A method for fabricating a double-cantilever beam crack growth sensor, comprising the following steps:
forming a block of an alloy of a first type; and
weld depositing a predetermined thickness of a weld alloy on top of said block of said alloy of said first type to form a bi-metallic test block, said weld alloy having a composition different than that of said alloy of said first type, said block of said alloy of said first type forming a heat sink for said molten weld alloy during cooling such that during solidification, said molten weld alloy adopts a microstructure having dendrites directed substantially vertically upward.

10. The method as defined in claim 9, further comprising the step of:
welding a second block of said alloy of said first type on top of said solidified weld alloy to form a three-layer block.

11. The method as defined in claim 9, further comprising the step of:
machining said block of said alloy of said first type to form first and second cantilever beams comprising said alloy of said first type and a crack growth section made of said weld alloy having said dendritic microstructure wherein said dendrites are substantially parallel to the general direction in which said first and second cantilever beams extend.

12. The method as defined in claim 9, wherein said alloy of said first type is carbon steel and said weld alloy is a nickel-based alloy.

13. The method as defined in claim 9, wherein said alloy of said first type and said weld alloy are nickel-based alloys.

14. The method as defined in claim 13, wherein said alloy of said first type and said weld alloy have a nickel content of at least 72% and at least 59% respectively.

15. The method as defined in claim 13, wherein said alloy of said first type has a composition substantially similar to that of Alloy 600 and said weld alloy has a composition substantially similar to that of Alloy 182.

16. A method for fabricating a double-cantilever beam crack growth sensor, comprising the following steps:
forming a first block of a first type of nickel-based alloy;
depositing a predetermined thickness of a nickel-based weld alloy on top of said first block to form a bi-metallic test block, said weld alloy having a nickel-based composition different than that of said nickel-based alloy of said first type;
milling the top surface of said weld alloy of said test block;
preparing the milled top surface of said weld alloy for welding;
forming a second block of said nickel-based alloy of said first type;
welding said second block to said weld alloy to form a three-layer block; and
machining said three-layer block to form first and second cantilever beams comprising said nickel-based alloy of said first type and a crack growth section made of said weld alloy having a dendritic microstructure wherein the dendrites are substantially parallel to the general direction in which said first and second cantilever beams extend.

17. The method as defined in claim 16, wherein said weld alloy has a minimum of 59% nickel.

18. The method as defined in claim 17, wherein said alloy of said first type has a minimum of 72% nickel.

19. The method as defined in claim 18, wherein said alloy of said first type has a composition substantially similar to that of Alloy 600.

20. The method as defined in claim 17, wherein said weld alloy has a composition substantially similar to that of Alloy 182.

* * * * *